United States Patent
Dvash et al.

(10) Patent No.: US 11,660,023 B2
(45) Date of Patent: May 30, 2023

(54) FALL DETECTION SYSTEMS AND METHODS

(71) Applicant: VAYYAR IMAGING LTD., Yehud (IL)

(72) Inventors: Amit Dvash, Zoran (IL); Ronen Tur, Binyamina (IL); Ido Klemer, Givatayim (IL); Alon Keren, Tel-Aviv (IL); Tomer Zimmerman, Tel-Aviv (IL); Michael Orlovsky, Hod Hasharon (IL); Yuval Lomnitz, Herzeliya (IL); Tsachi Rosenhouse, Kiryat Ono (IL)

( * ) Notice: Subject to any disclaimer, the term of this patent is extended or adjusted under 35 U.S.C. 154(b) by 0 days.

(21) Appl. No.: 17/632,522

(22) PCT Filed: Dec. 23, 2020

(86) PCT No.: PCT/IB2020/062383
§ 371 (c)(1),
(2) Date: Feb. 3, 2022

(87) PCT Pub. No.: WO2021/130690
PCT Pub. Date: Jul. 1, 2021

(65) Prior Publication Data
US 2022/0283292 A1    Sep. 8, 2022

Related U.S. Application Data

(60) Provisional application No. 62/952,519, filed on Dec. 23, 2019, provisional application No. 62/952,525, (Continued)

(51) Int. Cl.
*A61B 5/11* (2006.01)
*G01S 13/88* (2006.01)
(Continued)

(52) U.S. Cl.
CPC ........... *A61B 5/1117* (2013.01); *A61B 5/1126* (2013.01); *A61B 5/746* (2013.01); *G01S 13/66* (2013.01); *G01S 13/88* (2013.01)

(58) Field of Classification Search
CPC ......... G01S 13/66; G01S 13/88; A61B 5/746; A61B 5/1116; A61B 5/1117; A61B 5/1126
See application file for complete search history.

(56) References Cited

U.S. PATENT DOCUMENTS

| 7,567,200 B1 * | 7/2009 | Osterweil | G01S 13/56 |
| | | | 342/28 |
| 2013/0002434 A1 * | 1/2013 | Cuddihy | G01S 13/18 |
| | | | 342/28 |

(Continued)

FOREIGN PATENT DOCUMENTS

| CN | 111627185 A | * | 9/2020 |
| TW | I653610 B | | 3/2019 |

*Primary Examiner* — Nathaniel J Kolb
(74) *Attorney, Agent, or Firm* — Alphapatent Associates, Ltd; Daniel J. Swirsky

(57) ABSTRACT

Fall detection systems and methods use radar chips to scan monitored regions such that data obtained by the scanning radar chip are processed to identify targets within the monitored region. Targets are tracked and profiled indicating their posture and fall detection rules are applied. Standard energy profiles and time dependent energy profiles are generated for various segments of the monitored region and compared to the current energy profile for each target segment of the monitored region. Anomalies are detected, false fall alerts filtered out and verified fall alerts are generated.

15 Claims, 14 Drawing Sheets

Related U.S. Application Data filed on Dec. 23, 2019, provisional application No. 62/952,536, filed on Dec. 23, 2019, provisional application No. 62/952,540, filed on Dec. 23, 2019, provisional application No. 62/954,502, filed on Dec. 29, 2019, provisional application No. 62/954,505, filed on Dec. 29, 2019, provisional application No. 62/954,506, filed on Dec. 29, 2019, provisional application No. 63/024,520, filed on May 14, 2020, provisional application No. 62/954,507, filed on Dec. 29, 2019.

(51) Int. Cl.
*G01S 13/66* (2006.01)
*A61B 5/00* (2006.01)

(56) References Cited

U.S. PATENT DOCUMENTS

2016/0377705 A1* 12/2016 Zack ............... A61B 5/7282
342/21
2020/0143656 A1 5/2020 Li et al.

* cited by examiner

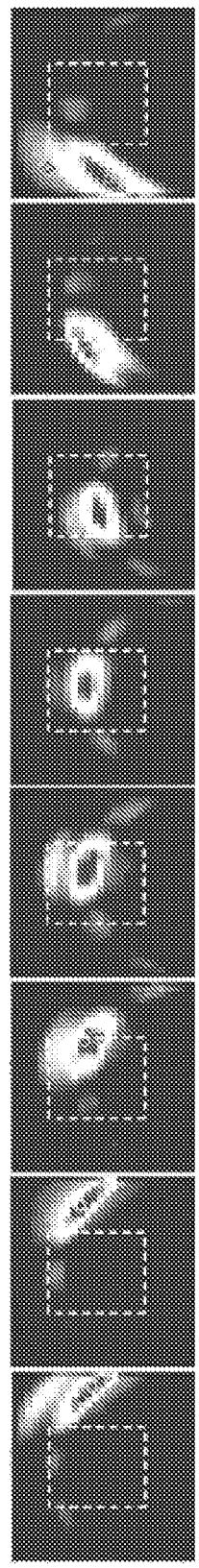

FALL DETECTION SYSTEMS AND METHODS

CROSS-REFERENCE TO RELATED APPLICATIONS

This application is a U.S. National Phase Application under 35 U.S.C. 371 of International Application No. PCT/IB2020/062383, which has an international filing date of Dec. 23, 2020, which claims the benefit of priority from U.S. Provisional Patent Application No. 62/952,519, filed Dec. 23, 2019, U.S. Provisional Patent Application No. 62/952,525, filed Dec. 23, 2019, U.S. Provisional Patent Application No. 62/952,536, filed Dec. 23, 2019, U.S. Provisional Patent Application No. 62/952,540, filed Dec. 23, 2019, U.S. Provisional Patent Application No. 62/954,502, filed Dec. 29, 2019, U.S. Provisional Patent Application No. 62/954,505, filed Dec. 29, 2019, U.S. Provisional Patent Application No. 62/954,506, filed Dec. 29, 2019, U.S. Provisional Patent Application No. 62/954,507, filed Dec. 29, 2019, and U.S. Provisional Patent Application No. 63/024,520, filed May 14, 2020, the contents of which are incorporated by reference in their entirety.

FIELD OF THE INVENTION

The disclosure herein relates to fall detection systems and methods. In particular the disclosure relates to the use of radar chips to identify that a subject within a monitored region may have fallen and further relates to alerting third parties.

BACKGROUND

The systems used for fall detection have important applications especially for senior citizens who live alone in homes and apartments and are isolated from people who could help them in an emergency. For such people, a fall, injury, or life threatening medical conditions can go undetected by family or support staff for an extended period of time. Some wearable and handheld devices are available which comprise of emergency call buttons, however, these need to be manually activated to alert others when assistance is needed. In case an elderly person falls down, he may not be in a position to activate the emergency button and call someone for help.

Another solution available for fall detection is through video camera surveillance. However, video camera surveillance is not a viable solution as it requires constant viewing of the video to know for fall detection or any help required by the person.

The need remains for improved fall detection systems. The current disclosure addresses this need.

SUMMARY OF THE EMBODIMENTS

According to one aspect of the presently disclosed subject matter, a fall detection system is introduced. The fall detection system may include a radar unit comprising at least one transmitter antenna connected to an oscillator and configured to transmit electromagnetic waves into a monitored region, and at least one receiver antenna configured to receive electromagnetic waves reflected by objects within the monitored region and operable to generate raw data. The fall detection system may further include a processor unit configured to receive raw data from the radar unit and operable to generate fall alerts based upon the received data; and a communication module configured and operate to communicate the fall alert to third parties.

Where appropriate, the processor unit may further comprise: a data filter configured to receive the raw data, and operable to process the raw data to remove data relating to reflections from static objects thereby generating filtered data; a tracker module configured to receive the filtered data from the data filter and operable to process the filtered data to identify moving targets and to track the location of the moving targets over time thereby generating target data; and a fall identification module configured to receive the target data from the tracker module and operable to process the target data by applying fall detection rules and further operable to generate fall alerts.

Additionally or alternatively, the data filter may comprise a memory unit, and a microprocessor, and the data filter is operable to: store a first set of raw data set from a first frame in the memory unit; store a second set of raw data set from a second frame in a memory unit following a selected time interval; and subtract first frame data from second fame data thereby generating filtered frame data.

Optionally, the tracker module comprises a peak detector, an associator and a target tracker. Accordingly, the peak detector may be configured to store filtered frame data, and operable to identity local maxima in each frame thereby generating peak data for the frame. The associator may be configured to store peak data for each frame and to receive tracking data from the target tracker. Thus, the associator may be operable to associate each peak with a target object, thereby generating target data; and the target tracker configured to receive the target data from each frame and operable to populate a target database with a location value and a speed value for each target in each frame, thereby generating tracking data.

Additionally or alternatively, the fall identification module may comprise a posture detector and a fall detector. The posture detector may be configured to store target data in a memory unit, to generate an energy profile for each target, and to apply posture selection rules thereby selecting a posture for each target, the posture detector further operable to store a posture history for each target in the memory unit. Optionally, the fall detector may be configured to access the posture history from the memory unit and to generate a fall alert if at least one target is identified as fallen and no target is identified as standing.

Additionally or alternatively, the processor unit comprises a pre-processor configured and operable to generate energy profiles for target segments of the monitored region and an anomaly detection module configured and operable to identify anomalous energy profiles.

Optionally, the system may include a profile database and the pre-processor may comprise an output unit operable to populate the profile database with standard energy profiles and time dependent energy profiles.

Where appropriate, the anomaly detector is operable to receive the current energy profile for each target segment from the output unit of the pre-processor and to compare the current energy profile with the corresponding time dependent energy profile stored in the profile database.

Optionally, the radar unit is configured to monitor an extended target region and the processor unit further comprises a gait classification module configured to receive the target data from the tracker module and operable to process the target data by applying gait classification rules and further operable to calculate a gait speed of a subject within the extended target region.

It is another aspect of the current disclosure to teach a method for fall detection comprising the steps: providing at least one radar unit comprising at least one transmitter antenna connected to an oscillator, and at least one receiver antenna configured to receive electromagnetic waves; providing at least one processor unit configured to receive raw data from the radar unit and operable to generate fall alerts based upon the received data; providing a communication module configured and operate to communicate a fall alert to third parties; transmitting electromagnetic waves into a monitored region; receiving electromagnetic waves reflected from objects in the monitored region; transferring multiple frames of raw data to processor unit; removing static objects from the frames of raw data; identifying moving targets in filtered data; tracking the moving targets over time; assigning posture to the targets; storing a posture history in a memory unit; applying fall detection rules; and generating a fall alert if a fall is detected.

Optionally the step of removing static objects from the frames of raw data comprises: collecting raw data from a first frame; collecting raw data from a second frame; and subtracting first frame data from the second frame data.

Additionally or alternatively, the step of identifying moving targets in filtered data comprises detecting local maxima within each frame of filtered data, and associating each local maximum with a target object.

Optionally, the step of identifying moving targets in filtered data may include: setting a peak detection threshold; detecting local maxima within each frame of filtered data; defining a stain region for each the local maximum; selecting peaks by selecting only local maxima having an amplitude above the peak detection threshold and which do not lie within the stain region of a larger local maximum; and associating each selected peak with a target object.

Where appropriate, the step of tracking the moving targets over time may comprise recording a location values for each target in each frame; and recording a speed values for each target in each frame. Additionally or alternatively, the step of tracking the moving targets over time comprises: recording a location values for each target in each frame; recording a speed values for each target in each frame; predicting an expected value for a target in each frame; and comparing expected value for each target with measured value for each target.

Optionally, the step of assigning posture to the targets comprises generating energy profile for each target; applying posture selection rules; and selecting a current posture. Variously, the step of assigning posture to the targets comprises generating an energy profile for each target by assigning: a first value for amplitude of reflected energy from an upper region or the target; a second value for amplitude of reflected energy from a middle region or the target; and a third value for amplitude of reflected energy from a lower region or the target; and wherein the step of applying fall detection rules comprises triggering a fall event when any target has an associated third value is higher than both the first value and the second value. Accordingly, the method may include generating a fall alert only if no other target has been identified with a standing posture during a previous time interval. Furthermore, the method may include generating a fall alert only if no target is identified having an associated middle value higher than both the first value and the lower value.

Where appropriate, the method may include: generating a set of energy profiles; segmenting the monitored region into target segments; recording activity within the target region for the duration of a learning period; for each target segment recording a time dependent profile distribution by recording the frequency of each energy profile during each hour of the learning period; and populating a profile database with standard energy profiles and time dependent energy profiles.

Additionally or alternatively, the fall detection method may further comprise: selecting a current profile for each target segment of the monitored region; communicating the current profile for each target segment to an anomaly detection module; comparing the current profile for each target segment with the time dependent profile distribution stored in the profile database; and identifying anomalous energy profiles.

Accordingly, the fall detection method may further comprise only generating a fall alert if both a fall is detected and an anomalous energy profile is detected.

BRIEF DESCRIPTION OF THE FIGURES

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the various selected embodiments may be put into practice. In the accompanying drawings:

FIGS. 9A-H—show a series of frames tracking a target which briefly disappears from view before returning; and FIGS. 10A-H—show a series of frames tracking a target which passes through an excluded region;

DETAILED DESCRIPTION

Figure 1:
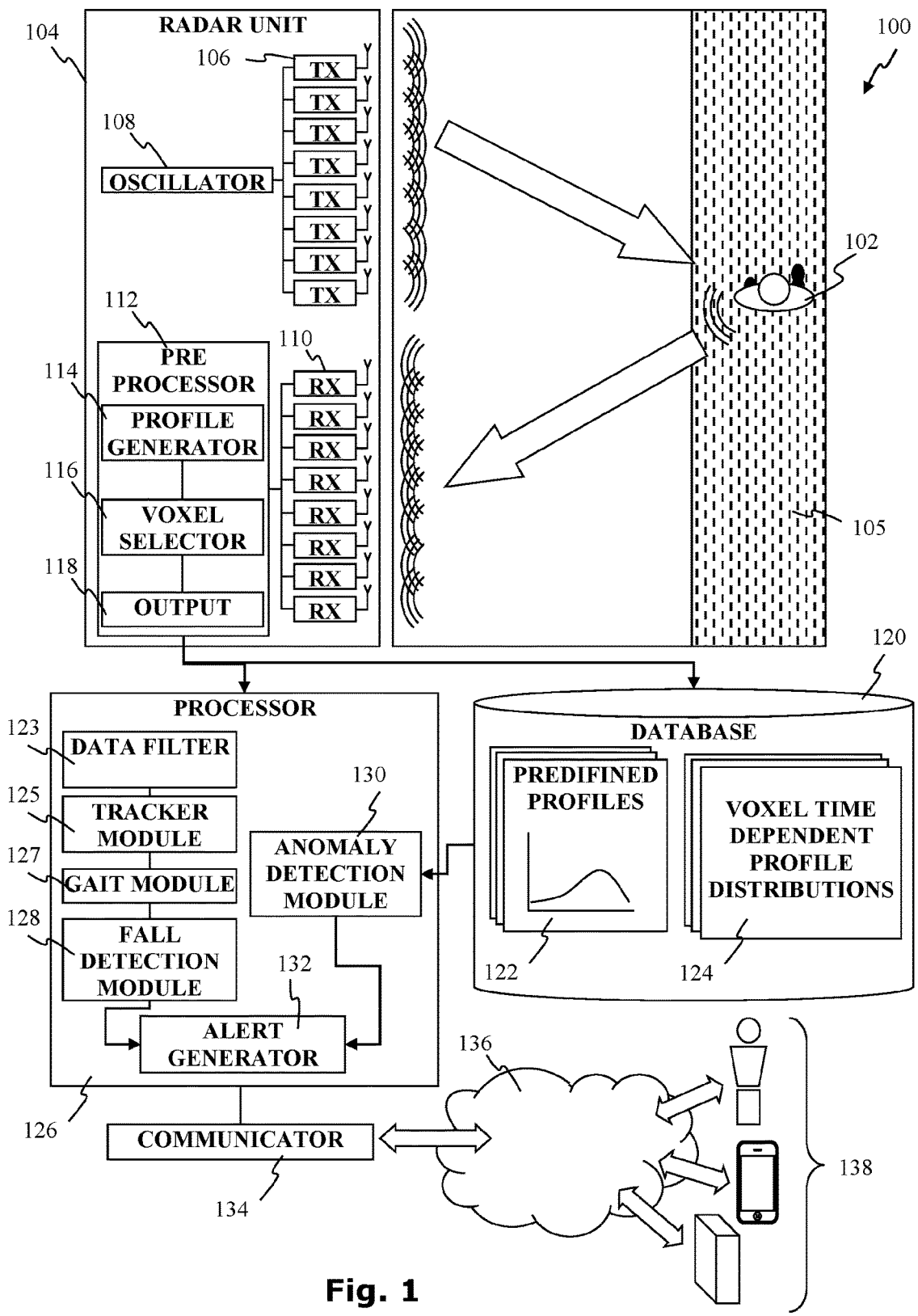
FIG. 1 is a schematic representation of a possible fall detection and alert system.

Aspects of the present disclosure relate to fall detection systems and methods. In particular the disclosure relates to the use of radar chips to scan a monitored region such as an enclosed room. The data obtained by the scanning radar chip may be processed to identify targets within the monitored region. The identified targets may be tracked and profiled to indicate their posture such that fall detection rules may be applied and fall events detected.

Certain image processing solutions are available which generate fall alerts using reflections in the target area from fallen objects. However, these image processing solutions do not differentiate between the fall of the subject person and other objects present in the region. For example, the reflected energy from a toilet bowl containing water is similar to that of a fallen person. Consequently, false alerts are generated with the fall of objects present in the room.

There is a need for improved solutions which block fall alerts if the reflected signal is not unusual for that section of the target area by identifying when the reflected signals are anomalous. Thus, further aspects of the present disclosure relate to systems and methods for identifying anomalies in fall detection and filtering fall alerts. Data obtained by the scanning radar chip may be processed to generate current energy profiles within the monitored region. The current energy profiles may be compared with time dependent energy profiles to detect anomalies in the fall events and filtering fall alerts.

As required, detailed embodiments of the present invention are disclosed herein; however, it is to be understood that the disclosed embodiments are merely examples of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As appropriate, in various embodiments of the disclosure, one or more tasks as described herein may be performed by a data processor, such as a computing platform or distributed computing system for executing a plurality of instructions. Optionally, the data processor includes or accesses a volatile memory for storing instructions, data or the like. Additionally or alternatively, the data processor may access a non-volatile storage, for example, a magnetic hard disk, flash-drive, removable media or the like, for storing instructions and/or data.

It is particularly noted that the systems and methods of the disclosure herein may not be limited in its application to the details of construction and the arrangement of the components or methods set forth in the description or illustrated in the drawings and examples. The systems and methods of the disclosure may be capable of other embodiments, or of being practiced and carried out in various ways and technologies.

Alternative methods and materials similar or equivalent to those described herein may be used in the practice or testing of embodiments of the disclosure. Nevertheless, particular methods and materials are described herein for illustrative purposes only. The materials, methods, and examples are not intended to be necessarily limiting. Accordingly, various embodiments may omit, substitute, or add various procedures or components as appropriate. For instance, the methods may be performed in an order different from described, and various steps may be added, omitted or combined. In addition, aspects and components described with respect to certain embodiments may be combined in various other embodiments.

Reference is now made to FIG. 1 which is a schematic representation of a possible fall detection and alert system 100. The fall detection system 100 includes a radar unit 104, a processor unit 126 and a communication module 134.

The radar unit 104 includes an array of transmitters 106 and receivers 110. The transmitter may include an oscillator 108 connected to at least one transmitter antenna TX or an array of transmitter antennas. 106 Accordingly the transmitter may be configured to produce a beam of electromagnetic radiation, such as microwave radiation or the like, directed towards a monitored region 105 such as an enclosed room or the like. The receiver may include at least one receiving antenna RX or an array of receiver antennas 110 configured and operable to receive electromagnetic waves reflected by objects 102 within the monitored region 105.

The processor unit, 126 which may include modules such as a data filter 123, a tracker module 125, a gait classification module 127 and a fall identification module 129, may be configured to receive data from the radar unit 104 and be operable to generate fall alerts based upon the received data. Where appropriate, a preprocessor 112 may be provided to process the raw data before transferring the data to the processor unit 126, as described herein.

The communication module 134 is configured and operable to communicate the fall alert to third parties 138. Optionally the communication module 134 may be in communication with a computer network 136 such as the internet via which it may communicate alerts to third parties 138 for example via telephones, computers, wearable devices or the like.

It is noted that the system may further include a radar based passive gait speed monitor 127 for use in the subject monitoring station which is schematically represented. The gait speed monitor 127 may be operable to generate a value for the gait speed of a subject passing along an extended target zone 105. The gait speed monitor includes at least one radar scanning arrangement and a processor unit.

The radar scanning arrangement 104 is configured to monitor the movement of a subject 102 over an extended range. The extended range 105 is of dimensions suitable for the measurement of speed of sustained gait along a path of say 4-8 meters. Thus, by way of example, it may be preferred to locate a scanning arrangement to cover movement in a target zone of say 5-6 meters squared.

Where appropriate a single radar scanning arrangement may be used to monitor the entire length of the extended target zone, however where required multiple scanning arrangements may be preferred. The radar typically includes at least one array of radio frequency transmitter antennas and at least one array of radio frequency receiver antennas. The radio frequency transmitter antennas are connected to an oscillator (radio frequency signal source) and are configured and operable to transmit electromagnetic waves towards the target region. The radio frequency receiver antennas are configured to receive electromagnetic waves reflected back from objects within the target region.

The processor unit 126, which may include modules such as a data filter 123, a tracker module 125 and a gait classification module 127, may therefore be configured to receive data from the radar unit and be operable to process the target data by applying gait classification rules and further operable to calculate a gait speed of the subject.

Figure 2:
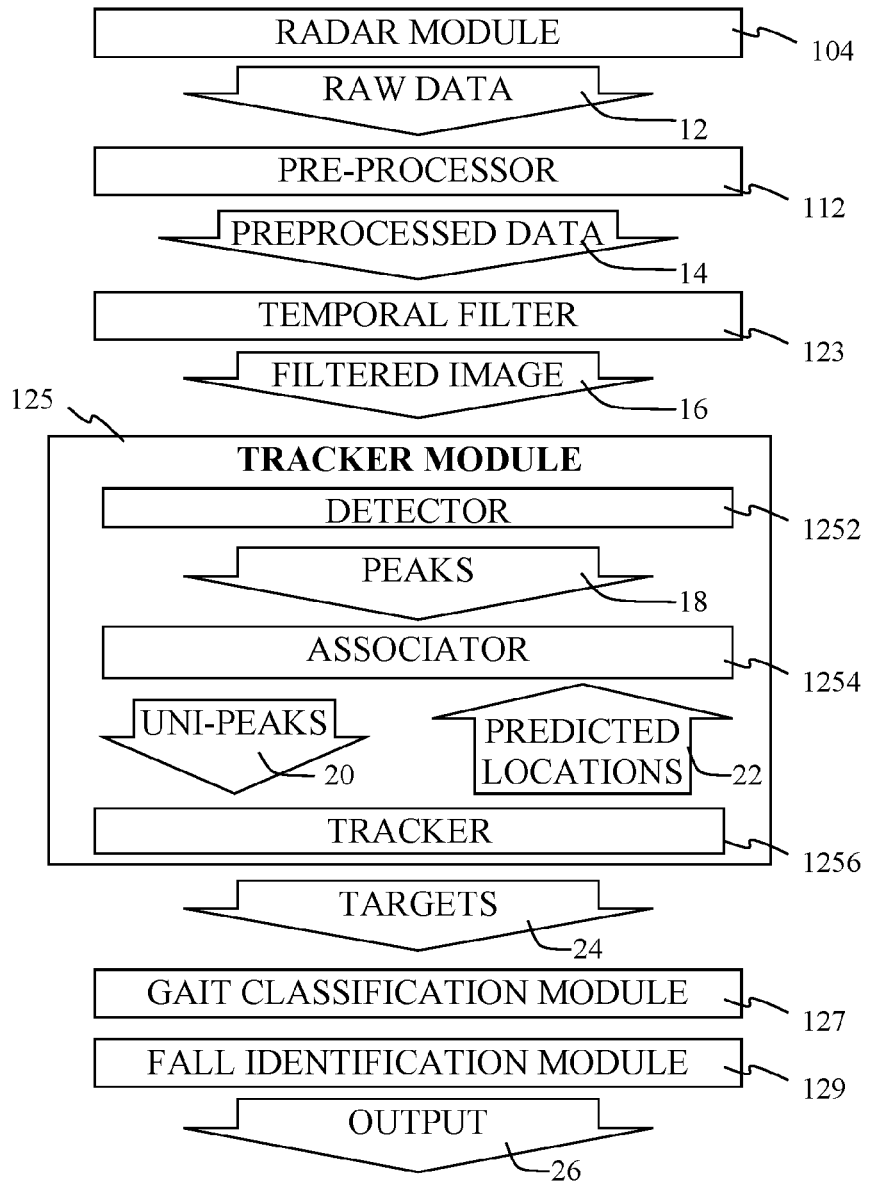
FIG. 2 is a schematic block diagram indicating data flow within a fall detection system.
Figure 7A:
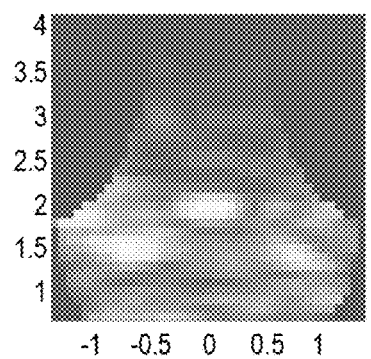
FIG. 7A is an example of an unfiltered frame in polar coordinates of data collected from the monitored region.

Reference is now made to the block diagram of FIG. 2 indicating possible data flow through the fall detection system 100. Raw data is generated by the radar module 104 which typically includes amplitude values for energy reflected at specific angles and ranges. The raw data 12 may be represented as images in polar coordinates such as shown in FIG. 7A for example. The preprocessor unit 112 may receive the raw data 12 from the radar module 104. The preprocessor unit 112 include a profile generator 114, a voxel selector 116 and an output 118.

Figure 7B:
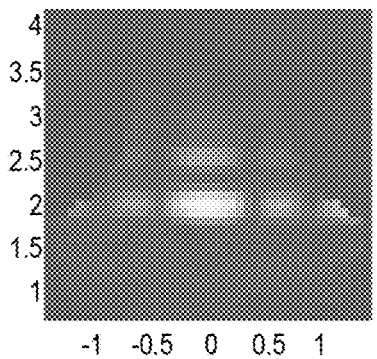
FIG. 7B is an example of a filtered frame in polar coordinates of data from which static objects have been removed.

The data filter 123 receives the raw data 12 directly from the radar module 104 or alternatively may receive preprocessed data 14 from the preprocessor unit 112. The data filter 123 may include a temporal filter operable to process the raw data 12 in order to remove all data relating to reflections from static objects. The filter 123 may thereby generate a filtered image 16 such as shown in FIG. 7B which includes only data pertaining to moving objects within the monitored region with background removed.

In certain examples, the data filter 123 may include a memory unit, and a microprocessor. Accordingly, the data filter 123 may store in the memory unit both a first set of raw data set from a first frame and a second set of raw data set from a second frame following a time interval. The microprocessor may be operable to subtract the first frame data from the second fame data thereby generating the filtered frame data. Other methods for filtering data will occur to those skilled in the art.

The filtered image data 16 may be transferred to a tracker module 125 operable to process the filtered image data 16 in order to identify moving targets with the data and to track the location of the identified moving targets over time thereby generating target data 24.

Figure 7C:
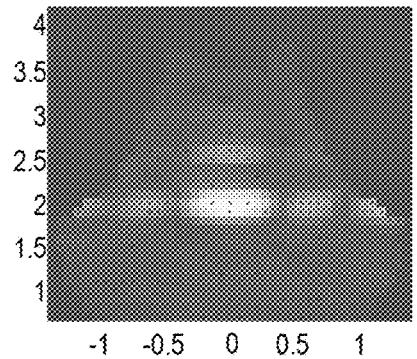
FIG. 7C represents the filtered data in polar coordinates indicating locations of local maxima.

The tracker module 125 may include a detector 1252, an associator 1254 and a tracker 1256 and is operable to generate data 24 relating to targets within the monitored region. The detector 1252 receives the filtered image data 16 from the temporal filter 123 and processes the filtered image data 16 to detect local maxima peaks 18 within its energy distribution. FIG. 7C shows an example of a filtered data image 16 indicating locations of local maxima peaks.

Figure 7D:
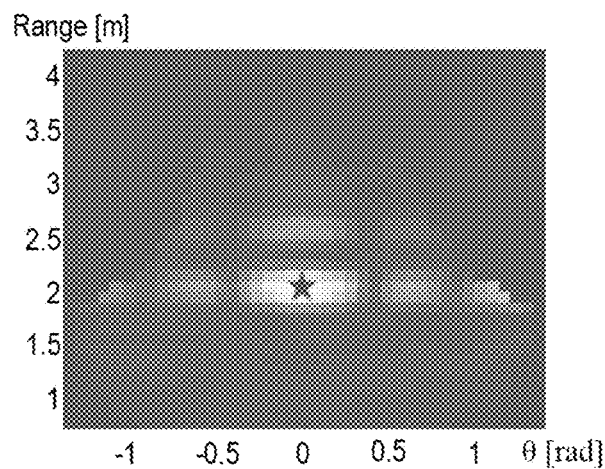
FIG. 7D represents the filtered data in polar coordinates indicating the location of the strongest local maximum peak.
Figure 7E:
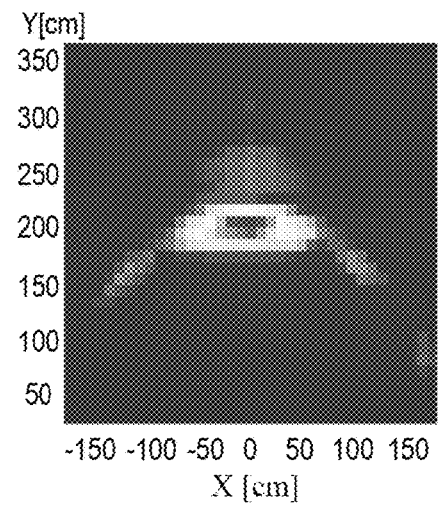
FIG. 7E represents the filtered data transformed into Cartesian coordinates.

The peaks data 18 may be transferred to the associator 1254. The associator 1254 is operable to store the peak data 18 for each frame in a memory element and to associate each peak with a target object and further generating a single peak location (uni-peak) for each target. FIG. 7D represents the filtered data indicating the energy distribution and the location of the uni-peak in polar coordinates. Typically the polar coordinates may be converted into Cartesian coordinates such as shown in FIG. 7E.

Figure 8A:
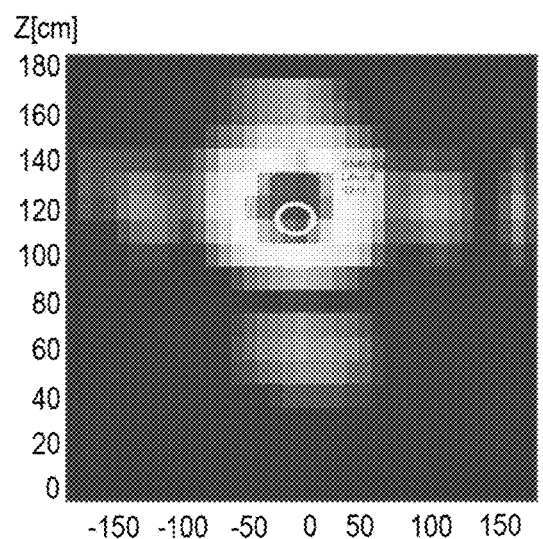
FIGS. 8A and 8B are images indicating the expected and measured locations of a tracked peak in two frames of data.
Figure 8B:
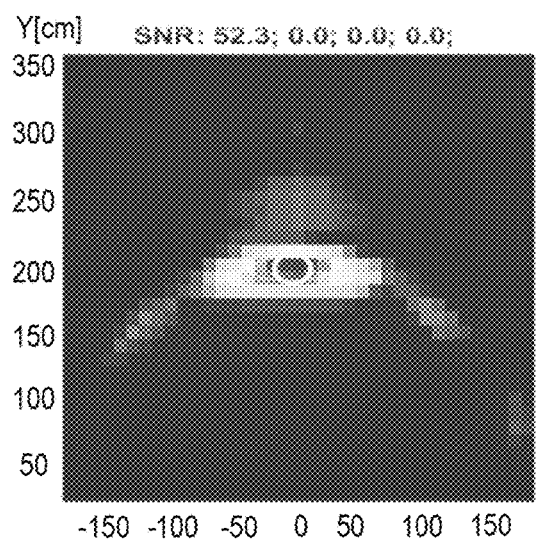

The tracker 125 may be configured to receive target data from each frame and be operable to populate a target database with a location value and a speed value for each target in each frame, thereby generating tracking data which may be used to calculate predicted locations 22 for each target in each frame. By way of example, FIGS. 8A and 8B are images indicating the expected and measured locations of a tracked peak in two frames of data;

The associator 1254 may be further operable to receive tracking data from a target tracker 1256. Accordingly when a uni-peak 20 coincides with the expected location of an existing target the peak may be associated with that existing target. Alternatively, where the location of the peak does not coincide with any tracked target the peak may be associated with a new target.

Target data 24 may be transferred to a gait classification module 127 and/or a fall identification module 129 operable to process the target data 24 by applying fall detection rules and to generate fall alert outputs 26 where required.

According to some examples, the fall identification module 129 includes a posture detector and a fall detector. The posture detector may be configured to store target data in a memory unit, to generate an energy profile for each target, and to apply posture selection rules thereby selecting a posture for each target. The posture detector may be further operable to store a posture history for each target in the memory unit. The fall detector may then access the posture history from the memory unit and generate a fall alert if at least one target is identified as fallen.

Figure 3:
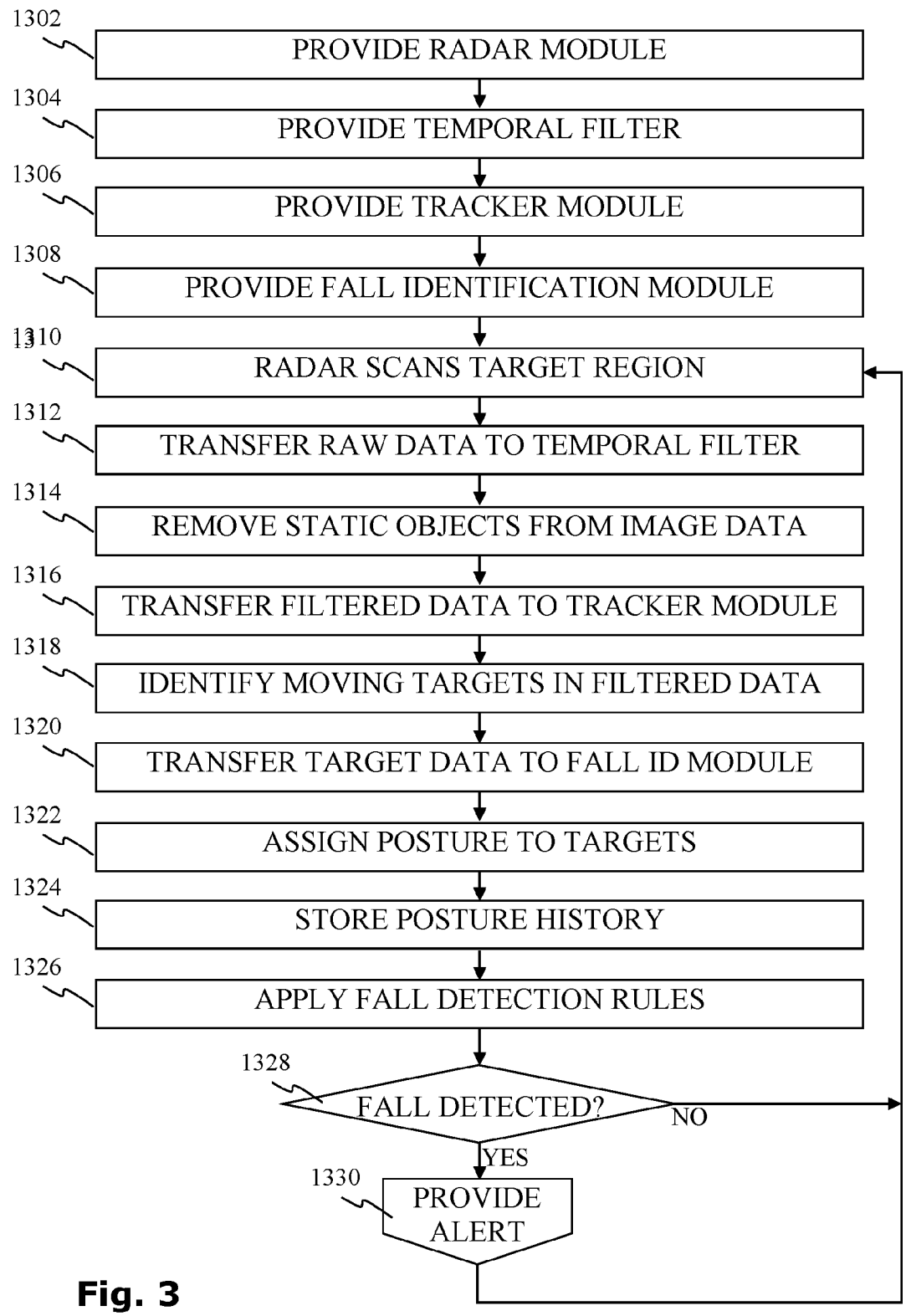
FIG. 3 is a flow chart representing actions of a fall detection method.

Referring now to the flowchart of FIG. 3, a method is taught for fall detection using systems such as described above. The method may include: providing a radar unit 1302 such as described herein, providing at least one processor unit configured to receive raw data from the radar unit and operable to generate fall alerts based upon the received data and providing a communication module configured and operated to communicate a fall alert to third parties. Optionally providing the processor may include providing a temporal filter 1304, providing a tracker module 1306 and providing a fall identification module 1308 such as described above.

The method may further include: the radar scanning the target region 1310, for example by transmitting electromagnetic waves into a monitored region and receiving electromagnetic waves reflected from objects in the monitored region; transferring multiple frames of raw data to the processor unit 1312; removing static objects from the frames of raw data 1314; transferring filtered data to the tracker module 1316, identifying moving targets in filtered data 1318; transferring target data to the fall identification module 1320; tracking the moving targets over time; assigning posture to the targets 1322; storing a posture history in a memory unit 1324; applying fall detection rules 1326; and generating a fall alert 1330 if a fall is detected 1328.

Figure 4:
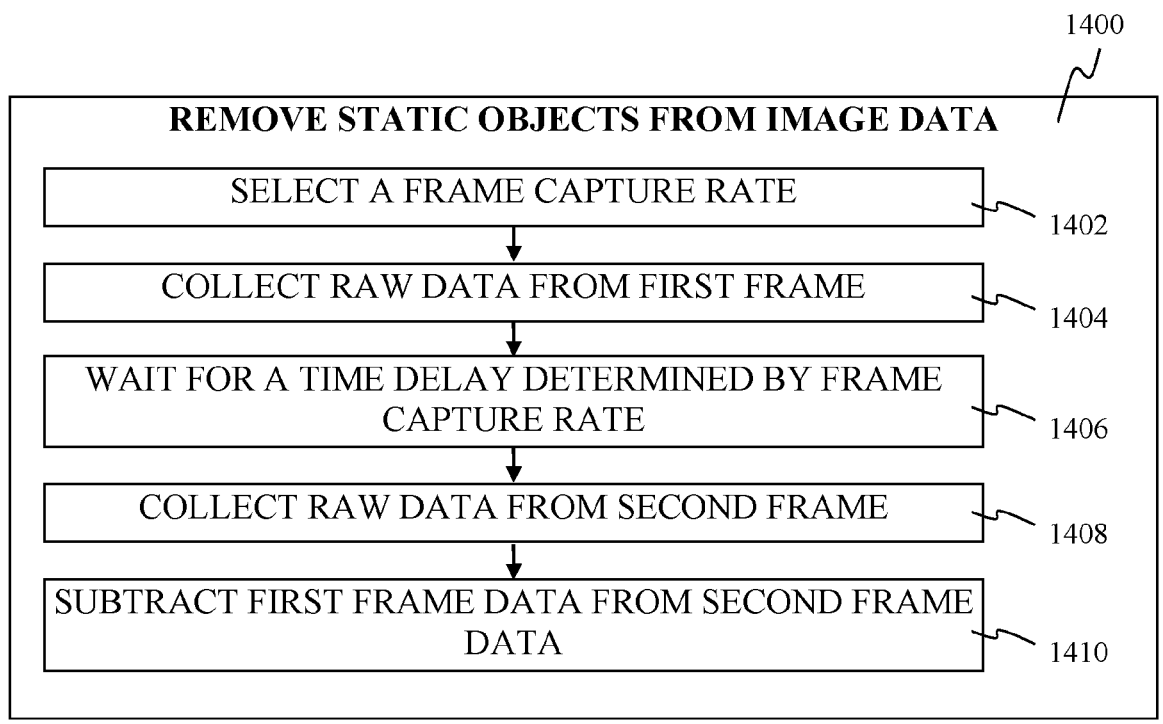
FIG. 4 is a flow chart representing possible actions for removing static objects from image data.

With reference to the flowchart of FIG. 4, which represents possible actions for removing static objects from image data 1400, a temporal filter may be applied to select a frame capture rate 1402, to collect raw data from a first frame 1404; to wait for a time delay, perhaps determined by frame capture rate 1406; to collect raw data from a second frame 1408; and to subtract first frame data from the second frame data 1410. In this way a filtered image may be produced from which static background is removed and the only moving target data remain.

Figure 5:
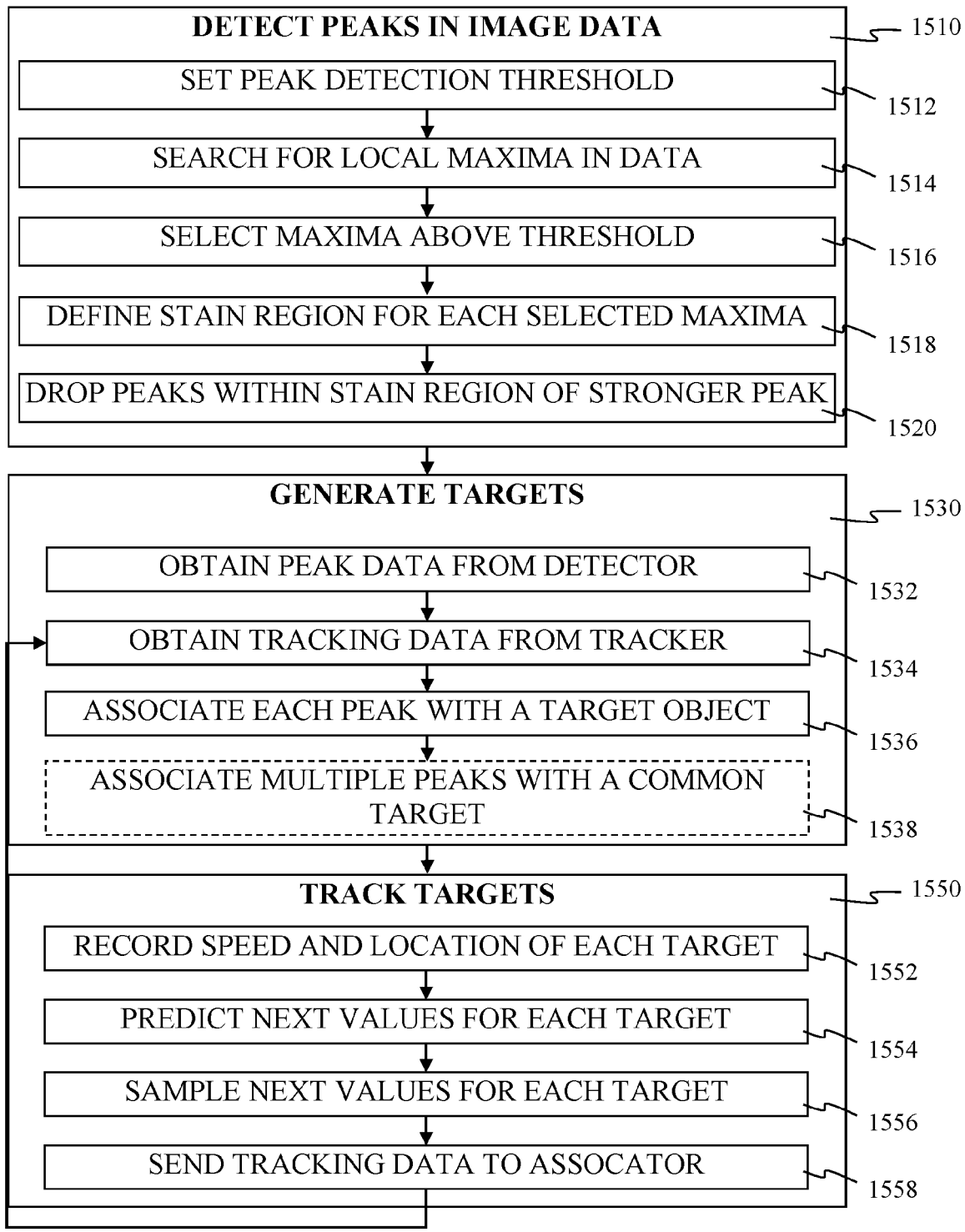
FIG. 5 is a flow chart representing possible actions for generating and tracking targets within data collected from the monitored region.

Referring now to the flowchart of FIG. 5 possible actions are represented for generating 1530 and tracking targets 1550 within data collected from the monitored region.

The method may include detecting local maxima within each frame of filtered data 1510 and associating each local maximum with a target object.

The step of identifying moving targets in filtered data may include: setting a peak detection threshold 1512; detecting local maxima within each frame of filtered data 1514; defining a stain region for each of the local maxima 1518; selecting peaks by selecting only local maxima having an amplitude above the peak detection threshold 1516 and which do not lie within the stain region of a larger local maximum 1520.

Peak data may be obtained from the detector 1532 and tracking data may be obtained from the tracker 1534. Accordingly, each selected peak may be associated with a target object 1536. Optionally multiple peaks may be associated with a common target 1538.

Where appropriate, if a peak coincides with the expected location of an existing target the peak may be associated with that existing target. Alternatively, where the location of the peak does not coincide with any tracked target the peak may be associated with a new target.

The moving targets may be tracked over time 1550 by recording in a tracking memory or database a location value for each target in each frame; recording a speed value for each target in each frame 1552; predicting an expected value for a target in each frame 1554; sampling the next values for each target 1556, sending tracking data to associator 1556 and comparing the expected value for each target with the measured value for each target.

Reference is now made to FIGS. 9A-H which show a series of frames of filtered data. The series of frames indicate a moving target within the monitored region which is tracked over time. The tracked target is marked in each frame by a small circle indicating the targets tracked location. It is particularly noted that in FIG. 9G, the target's location is not indicated. Such a scenario may occur for example, when the moving object within the monitored region, which is represented by the target in the data, moves behind a stationary object. The data filter would typically remove the stationary object from the frame, thereby rendering the moving object invisible in the filtered data.

Note that although the object is lost in the filtered data, the associated target is not removed from the tracking database. Rather the missing target is retained and its expected location is calculated for subsequent frames such that when the object peak returns to view such as in FIG. 9H, the peak is again associated with the original target.

Reference is now made to FIGS. 10A-H which show a series of frames of filtered data. The series of frames indicate a moving target which passes through an excluded region within the monitored region, which is marked by a dashed rectangle in each frame. It may be useful to exclude certain regions from the data when, for example, a persistently moving object interfered with data. Such a persistently moving object may be for example a swaying pendulum, a rippling curtain or the like.

Note that when a tracked object passes within the excluded region, such as shown in FIGS. 10D-F, the object is no longer physically monitored but the associated target is not removed from the tracking database. Rather the missing target is retained and its expected location is calculated for subsequent frames such that when the object peak passes out of the excluded region, such as in FIG. 10G, the peak is again associated with the original target.

Figure 6:
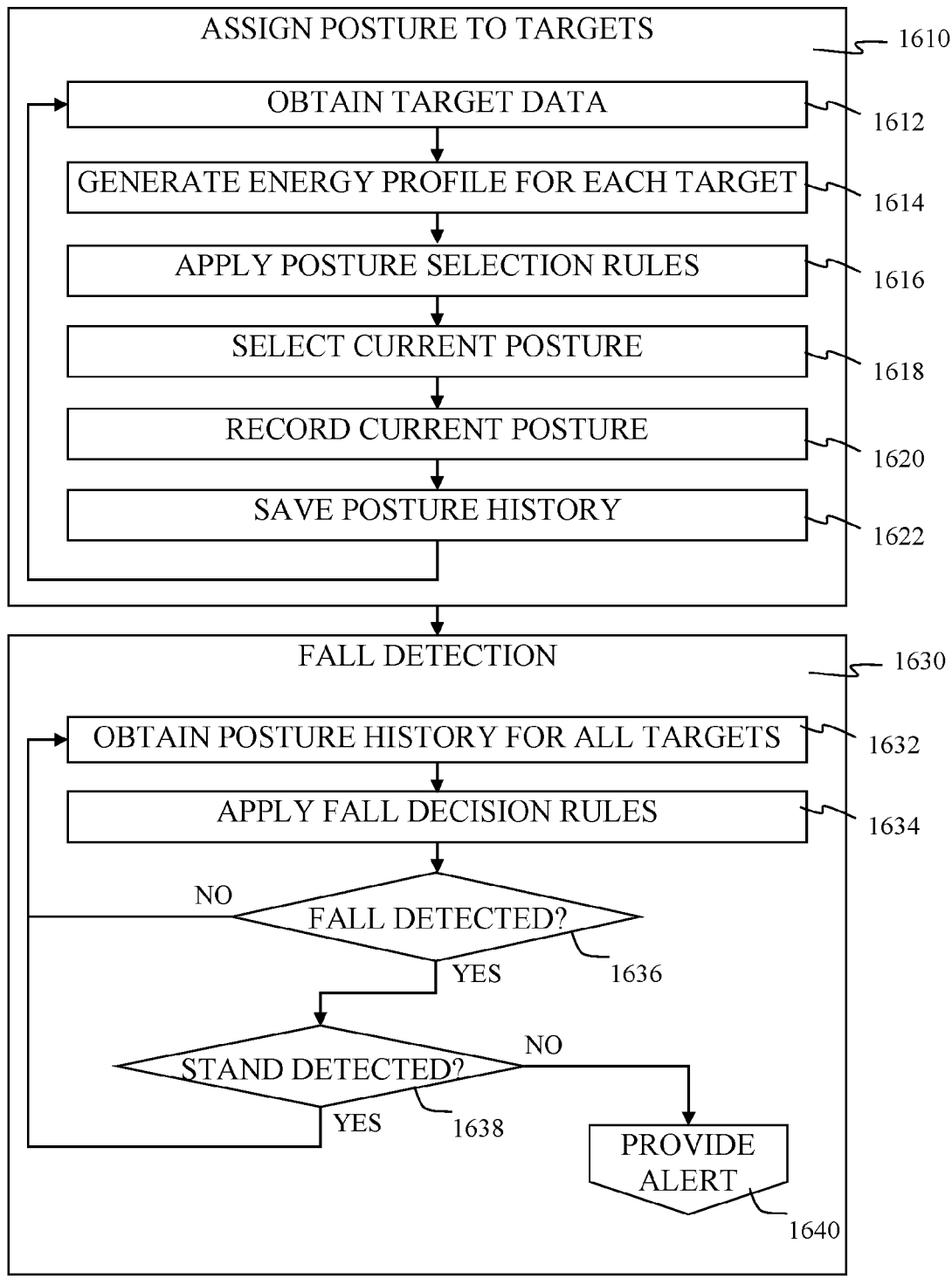
FIG. 6 is a flow chart representing possible actions for detecting fall events within the monitored region.

Referring now to the flowchart of FIG. 6 representing possible actions for detecting fall events within the monitored region, a phase of assigning posture to the targets 1610 may include: obtaining target data 1612; generating energy profile for each target 1614; applying posture selection rules 1616; selecting a current posture 1618; recording current posture 1620 and saving current posture in a posture history 1622

A fall detection phase 1630 may include obtaining the posture history of all targets 1632; applying fall decision rules 1634 and providing an alert 1640 only if a fall is detected in one target 1636 and no other target has been assigned a standing posture 1638.

Figure 11:
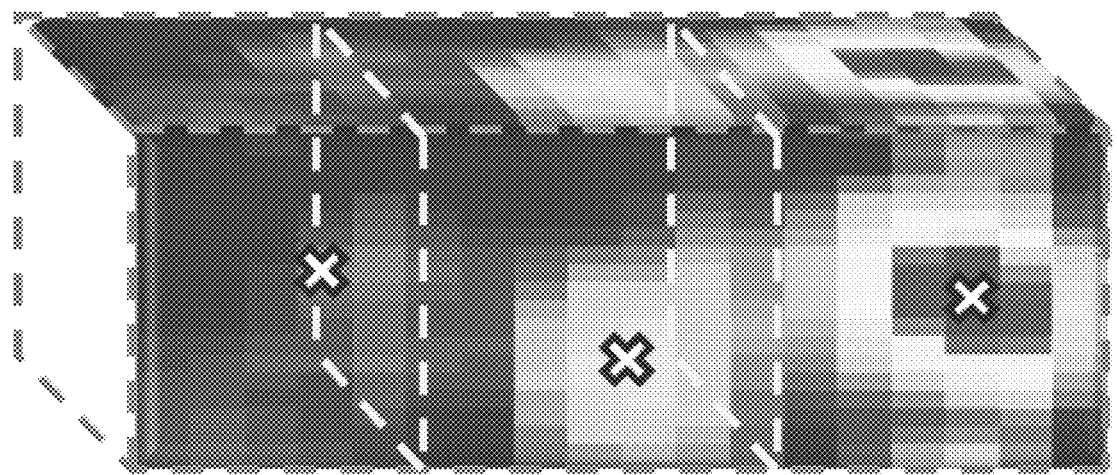
FIG. 11 shows a possible three dimensional energy profile for a target divided into an upper region, a middle region and a lower region.

Referring now to FIG. 11, which shows a possible three dimensional energy profile for a target where appropriate, generating an energy profile for each target includes assigning a first value for amplitude of reflected energy from an upper region or the target; assigning a second value for amplitude of reflected energy from a middle region or the target; and assigning a third value for amplitude of reflected energy from a lower region or the target.

Figure 12A:
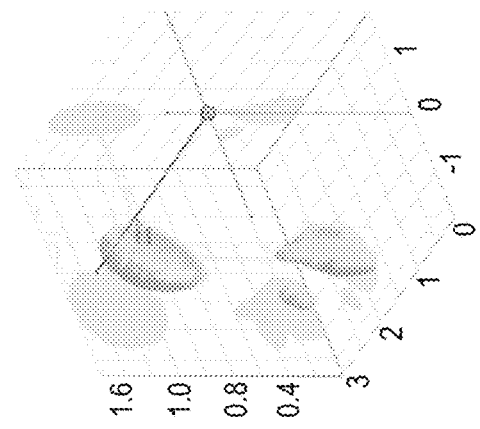
FIG. 12A shows a three dimensional energy profile characteristic of a standing target.
Figure 12B:
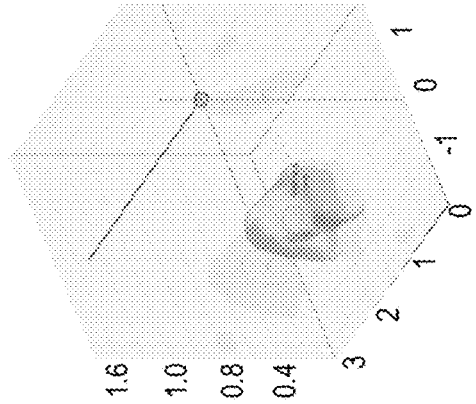
FIG. 12B shows a three dimensional energy profile characteristic of a non-lying target.
Figure 12C:
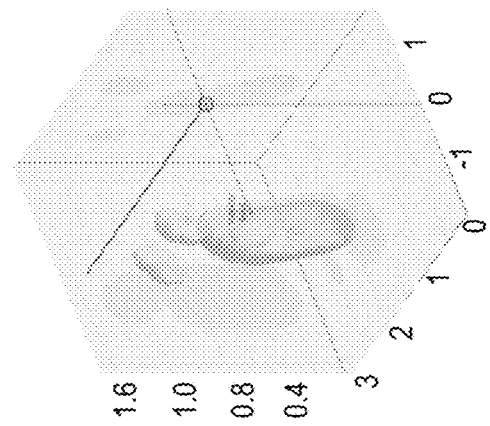
FIG. 12C shows a three dimensional energy profile characteristic of a fallen target.
Figure 12D:
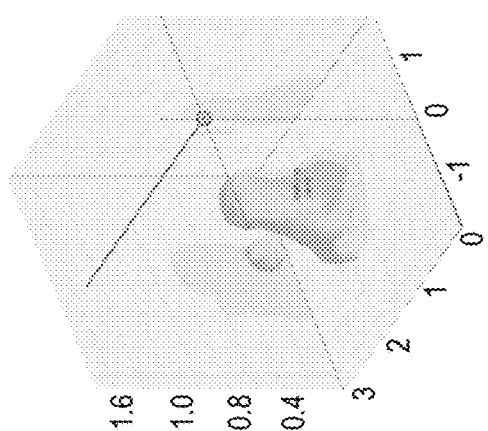
FIG. 12D shows a three dimensional energy profile characteristic of a persistent fallen target.

Characteristic energy profiles may be defined for various postures for example a fallen or lying posture may be identified when the third value for the amplitude is higher than both the first value and the second value such as illustrated in FIGS. 12C and 12D. Such a posture may generate a fall alert.

A standing posture may be identified for example when the first value, second value and third values have similar amplitudes such as shown in FIG. 12A.

A posture may be simply classified as not lying where the third value for the amplitude is not higher than both the first value and the second value such as shown in FIG. 12B.

Referring back now to FIG. 1, the system 100 may further be operable to detect anomalies so as to more accurately detect falls and to generate alerts. Accordingly, the radar unit 104 also includes a pre-processor unit 112 which processes the data received from the receiver 110.

The pre-processor unit 112 includes a profile generator 114 configured to generate energy profiles for a target area. The profile generator 114 generates a set of standard energy profiles 122 and time dependent energy profiles 124 for various segments of the target area. Where appropriate, such energy profiles 122 may be generated in advance and preloaded into the unit, as required. The set of standard energy profiles 122 and time dependent energy profiles 124 are stored in the database 120. The pre-processor unit 112 also includes a segment selector 116 configured to select a target segment of interest in the monitored region 102 by selecting radiations received within a given azimuth range (of the angles measured along the horizontal) at a given depth range measured by the time taken by reflections to arrive at the receiving antennas 110. The profile generator 114 also generates a current energy profile for each target segment of the monitored region 102 selected by the segment selector 116. An output unit 118 sends the standard energy profiles 122 and time dependent energy profiles 124 to the database 120 and the current energy profile of each target segment to the processing unit 126 for anomaly detection and filtering alerts. The output unit 118 is also configured to send the raw data received by the receiver 110 to the processing unit 126. The output unit 118 also sends the selected target segments of interest to the processing unit 126 for anomaly detection.

The processing unit 126 includes a fall detection module 128 which may be configured to receive data from the output unit 118 and operable to generate fall alerts based upon the fall detection rules. The anomalous fall alerts are filtered by an anomaly detection module 130 which may be configured to receive the current energy profile for a selected target segment from the output unit 118 and the set of standard energy profiles 122 and time dependent energy profiles 124 from the database 120. For the selected target segment, the current energy profile is compared with the corresponding time dependent energy profile and anomalous fall alerts are filtered out. An alert generator 132 then generates fall alerts and sends it to the communication devices (not shown) of the intended recipients. The fall alerts may be communicated through a communication network to the recipients on their smartphones, computers, laptops, wearable devices like smart-watch, electronic bands, wearable collar, etc. The communication networks include a Bluetooth network, a Wired LAN, a Wireless LAN, a WiFi Network, a Zigbee Network, a Z-Wave Network or an Ethernet Network. The alert generator 132 may produce alerts in form of a text message, an image, a short video message, vibration signals, a buzzer, a beeper, a bell, a bleeper, a chirper and combinations thereof. The audio/vibration means provided above for generating alerts are exemplary in nature and should not limit the scope of the invention.

Figure 13A:
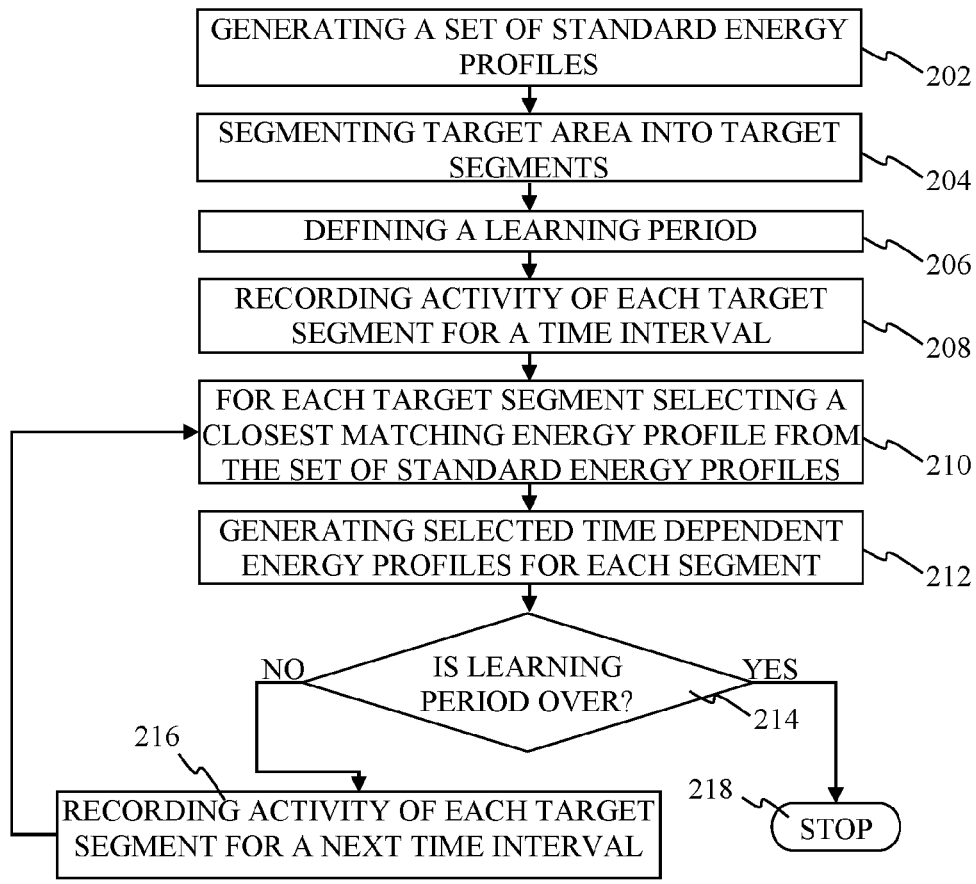
FIG. 13A is a schematic flowchart illustrating an exemplary method for populating a database with time dependent energy profiles according to an aspect of the invention.
Figure 14:
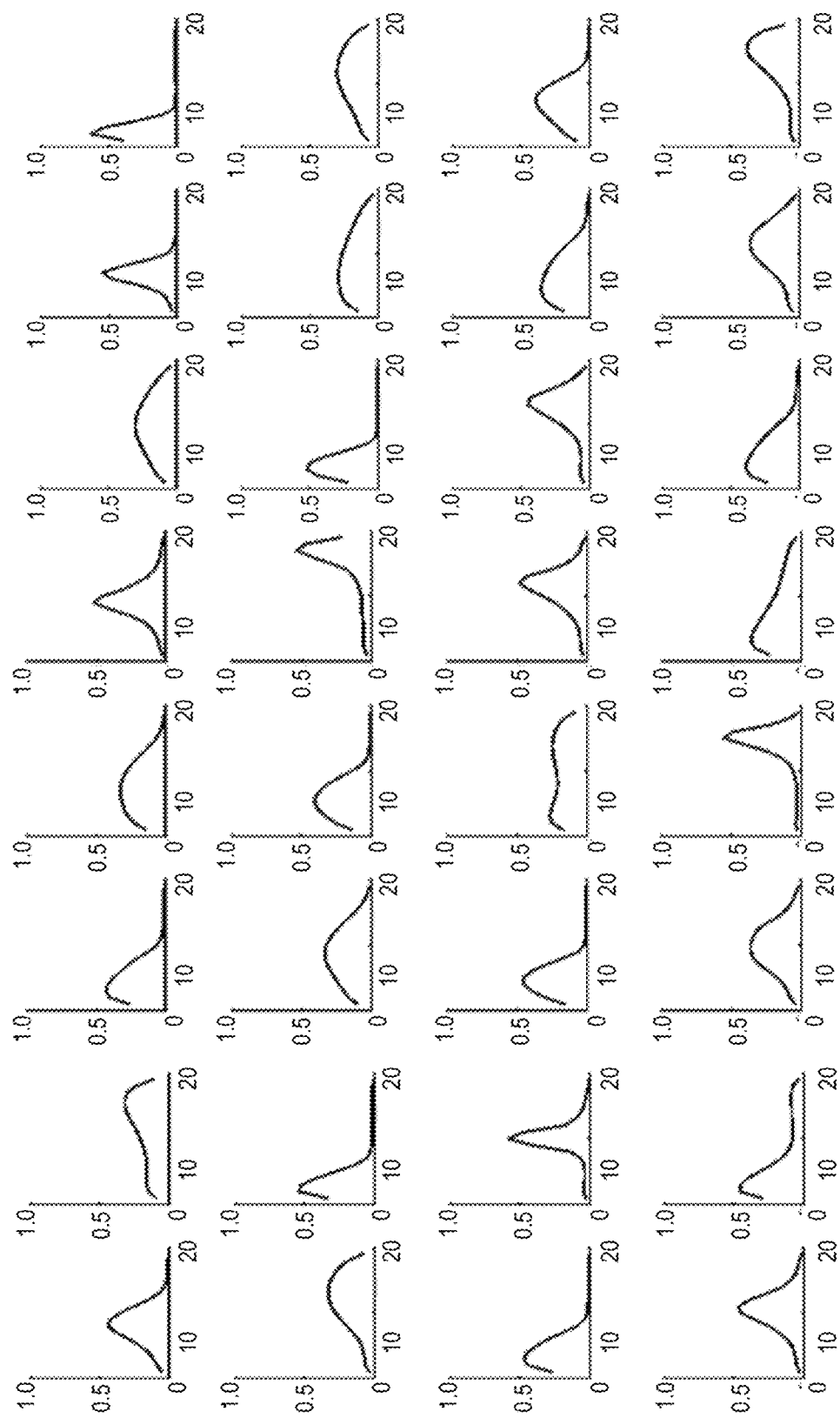
FIG. 14 shows a set of standard energy profiles for a target area.

Referring to FIG. 13A which illustrates an exemplary method for populating a database with time dependent energy profiles. The time dependent energy profile for each section of the target area shows the relative likelihood of each of the set of energy profile being selected at a given time of day. The process starts at step 202 at which a set of standard energy profiles 122 are generated and stored in the database 120. The set of standard energy profiles 122 characterize the expected energy distribution associated with a subject in a different pose (standing, sitting, lying, walking, bending over etc. . . . ). A set of 32 standard energy profiles of an exemplary subject are shown in FIG. 14. These standard energy profiles are generated from large sample of data collected over a large period of time.

At step 204, the target area is segmented into a number of target segments by the segment selector 116. A learning period for collecting time dependent data is defined at step 206. In an exemplary embodiment, a learning period of 48 hours is defined with time intervals of 1 hour. At step 208, for each time interval, activity of each target segment is recorded. The activity is recorded through the reflections received from the target segments by the receiver 110 of the radar unit 104. At step 210, the profile generator 114 selects a closest match for the target segment from the set of standard energy profiles and generates time dependent energy profiles 124 for each segment at step 212. The time dependent energy profiles 124 are stored in the database 120.

At step 214, it is determined if all time intervals of the learning period have been completed. It is noted that the system may continue gathering profiles in an ongoing manner during operation even after the learning period is over. Where required older data may be overwritten or purged. In this manner the previous 48 hours may always be divided into a number of time intervals, such as 24 or twelve time intervals as required.

Figure 15:
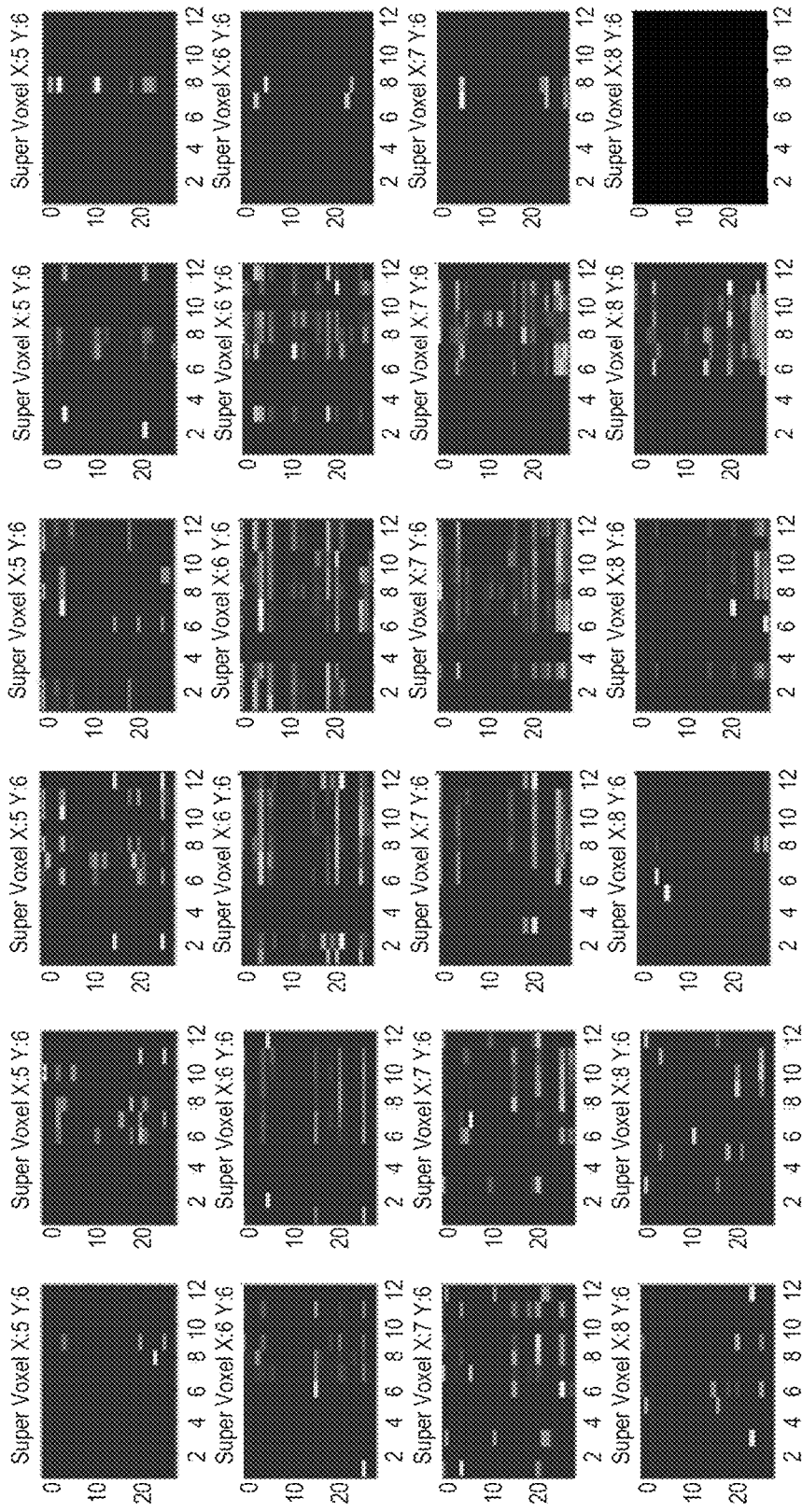
FIG. 15 shows a set of time dependent energy profiles for target segments of a target area.

If "yes", all time intervals of the learning period have been completed, then the process of populating the database 120 with time dependent energy profiles is completed and the process stops at step 218. Else, the activity of each target segment is recorded for the next time interval at step 216 and process repeats from step 210. FIG. 15 shows an exemplary set of time dependent energy profiles 124 for various target segments of a target area. The term "Super Voxel" herein refers to a "target segment" of the target area with 'X' and 'Y' coordinates defining the particular target segment.

Figure 13B:
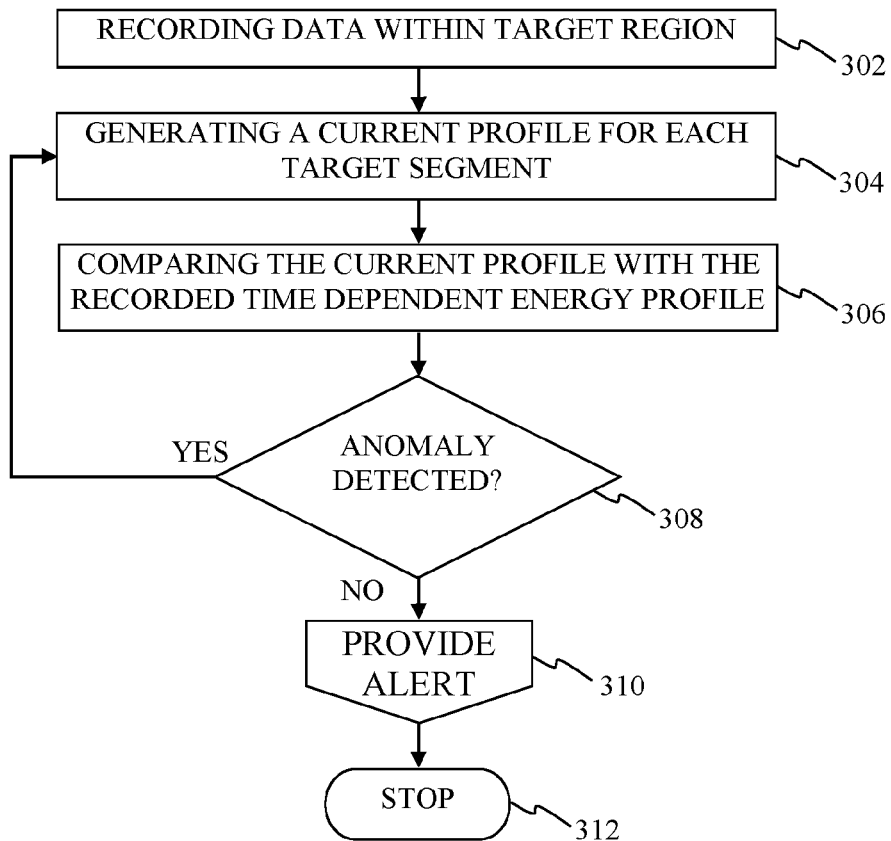
FIG. 13B is a schematic flowchart illustrating an exemplary method for anomaly detection and alert generation according to an aspect of the invention.

Reference is now made to FIG. 13B which is a schematic flowchart illustrating an exemplary method for anomaly detection in fall alerts and alert generation. In case a fall is detected in the target region 102 based on the fall detection rules, at step 302, data corresponding to target region 102 is recorded by the receiver 110 of the radar unit 104. For each target segment of the target area 102, a current energy profile is generated by the profile generator 114 and sent to the processing unit 126 by the output unit 118 at step 304. At step 306, the current energy profile is compared with the recorded time dependent energy profile 124 stored in the database 120. Based on the comparison, it is determined if an anomaly is detected in the fall detection at step 308. In case no anomaly is detected in the fall detection, an alert is generated and provided to the intended recipients through various means at step 310. In case an anomaly is detected in the fall detection, the fall alert if filtered out and process repeats from step 304. The process completes at step 312.

In an exemplary embodiment, the process of anomaly detection in fall alerts is explained using Kullback-Leibler (KL) Divergence which measures how a probability distribution differs from a reference probability distribution. A metric $M^i$ is defined by the KL Divergence as:

$$M^i(P_D^i \| P_W) \sum_v P_D^i \log(\frac{P_D^i}{P_W})$$

where, $P_W^i$ refers to time dependent energy profile distribution of a target segment; and $P_D$ refers to the current energy profile distribution of the target segment.

A threshold T is defined such that if $M^i < T$ there is no anomaly in the fall detection. Consequently, a fall alert is generated and sent to the intended recipients. Otherwise, if $M^i \geq T$ an anomaly is detected in the fall detection the fall detection is filtered out and no alert is generated.

Additionally or alternatively, an anomaly score may also be provided according to the confidence score based on the quality of information in the database and its diversity. A filter mechanism may be provided to perform a decision function base upon parameters such as the anomaly score and the like to further select appropriate alert generation.

It should be clearly understood that the process of anomaly detection in fall alerts explained using Kullback-Leibler (KL) Divergence is exemplary in nature and should not limit the scope of the invention. Any other suitable probability distribution function can be used for the purpose without limiting the scope of the invention.

Figure 16A:
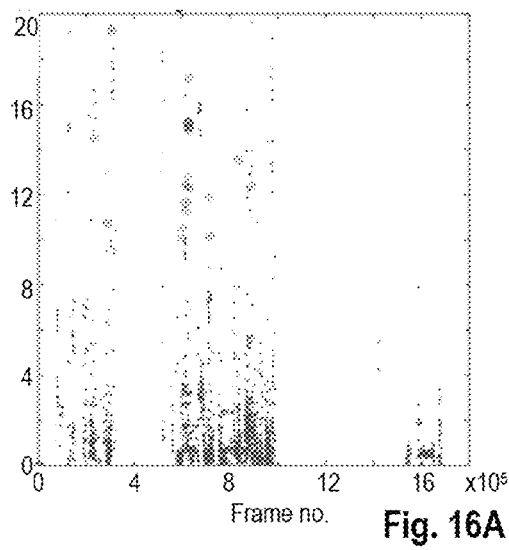
FIGS. 16A, 17A and 18A illustrate KL Divergence values over all time windows in case of normal behaviour in exemplary embodiments of the invention.
Figure 17A:
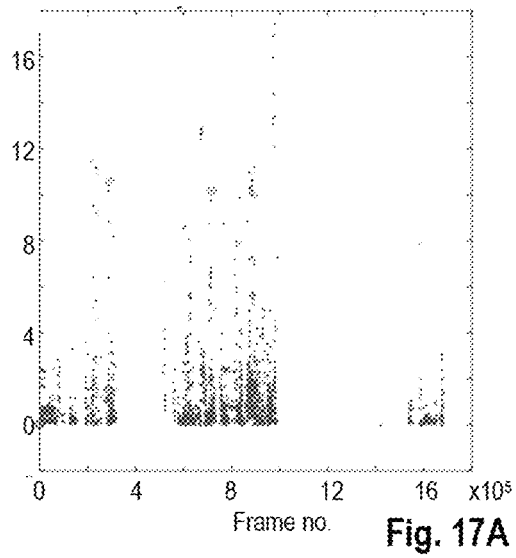
Figure 18A:
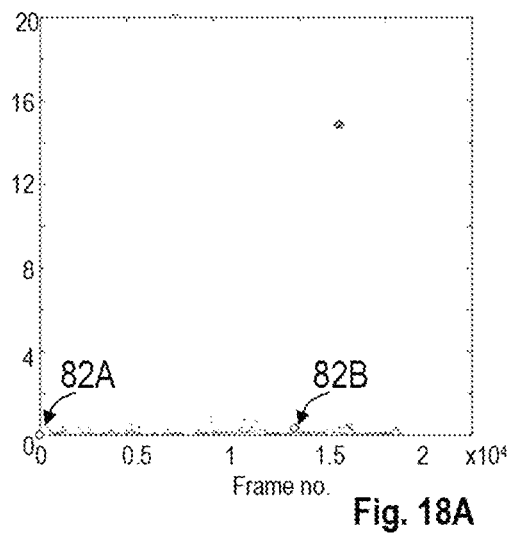

FIGS. 16A, 17A and 18A illustrate KL Divergence values over all time windows in case of normal behavior in exemplary embodiments of the invention.

Figure 16B:
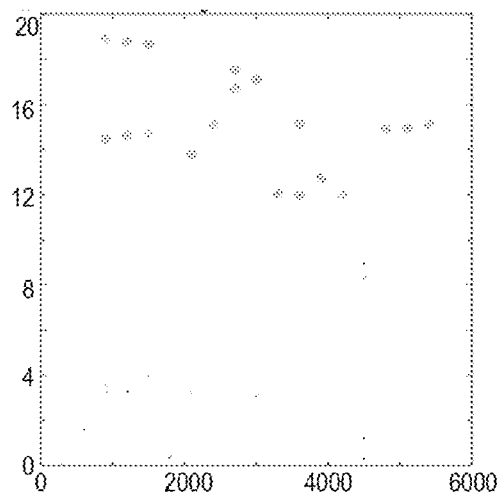
FIGS. 16B, 17B and 18B illustrate KL Divergence values over all time windows in case of actual falls in exemplary embodiments of the invention.
Figure 17B:
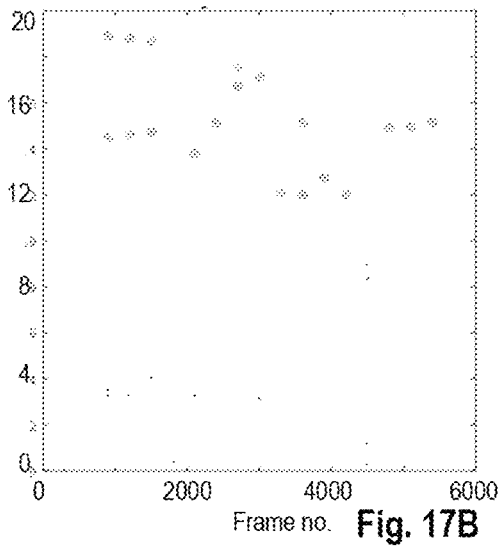
Figure 18B:
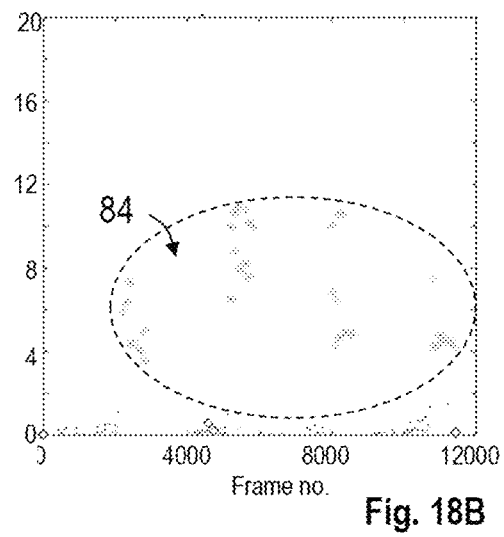

FIGS. 16B, 17B and 18B illustrate KL Divergence values over all time windows in case of actual falls in exemplary embodiments of the invention.

It is noted that the circled points in FIGS. 16A and 17A represent anomalies detected which do not correspond to actual falls. Such anomalies would not typically result in an alert being generated as they would not be accompanied by a fall detection event.

It is noted that the circled points in FIGS. 16B and 17B represent anomalies detected which correspond to actual falls. Such anomalies would typically be accompanied by a fall detection event and would therefore generate a fall alert.

FIGS. 16A and 16B represent divergence values recorded before the learning period was completed. By contrast, FIGS. 17A and 17B represent divergence values recorded after a learning period has been completed. Consequently more events are recorded as anomalous in FIG. 16A than in 17A although both these represent normal behavior.

Referring now to FIG. 18A, which shows KL divergence where no actual falls occur, it will be noted that although a number of fall detection events are recorded, as are circled in green, no corresponding anomaly was detected. Thus false positives are avoided.

By contrast, in FIG. 18B, where actual falls do occur, these generated fall detection events and are circled in green, it is noted that the events also correspond to anomalies. Accordingly, the fall detection alert is generated.

The systems and methods explained above provide an improvement to fall detection methodology by avoiding false positives.

Further features of the system include the capability to retain a long term memory for rare events, such as the operation of a washing machine or the like, which may otherwise be considered anomalies if only a 48 hour slice of memory is considered.

It is further noted that the system may classify zones within the target regions based upon the time dependent profiles. For example a zone may be identified to be a bed, if, say, a lying posture is detected over a long time mainly during night hours, or a toilet if, say, sitting and/or standing profiles are detected for characteristic short periods and so on. Such a classification system may form a basis for advanced room learning.

It is appreciated that certain features of the invention, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Although the invention has been described in conjunction with specific embodiments thereof, it is evident that other alternatives, modifications, variations and equivalents will be apparent to those skilled in the art. Accordingly, it is intended to embrace all such alternatives, modifications, variations and equivalents that fall within the spirit of the invention and the broad scope of the appended claims. Additionally, the various embodiments set forth hereinabove are described in terms of exemplary block diagrams, flow charts and other illustrations. As will be apparent to those of ordinary skill in the art, the illustrated embodiments and their various alternatives may be implemented without confinement to the illustrated examples. For example, a block diagram and the accompanying description should not be construed as mandating a particular architecture, layout or configuration.

Technical Notes

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

As used herein the term "about" refers to at least ±10%.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between. It should be understood, therefore, that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

The scope of the disclosed subject matter is defined by the appended claims and includes both combinations and sub combinations of the various features described herein above as well as variations and modifications thereof, which would occur to persons skilled in the art upon reading the foregoing description.

The invention claimed is:

1. A fall detection system comprising:
a radar unit comprising
at least one transmitter antenna connected to an oscillator and configured to transmit electromagnetic waves into a monitored region,
at least one receiver antenna configured to receive electromagnetic waves reflected by objects within the monitored region and operable to generate raw data,
a processor unit configured to receive raw data from the radar unit and operable to generate fall alerts based upon the received data, and
a communication module configured and operable to communicate the fall alert to third parties,
wherein said processor unit comprises
a data filter configured to receive said raw data, and operable to process the raw data to remove data relating to reflections from static objects thereby generating filtered data,
a tracker module configured to receive the filtered data from the data filter and operable to process the filtered data to identify moving targets and to track the location of the moving targets over time thereby generating target data, and
a fall identification module configured to receive the target data from the tracker module and operable to process the target data by applying fall detection rules and further operable to generate fall alerts, and
wherein said data filter comprises a memory unit, and a microprocessor, and the data filter is operable to
store a first set of raw data set from a first frame in the memory unit,
store a second set of raw data set from a second frame in a memory unit following a selected time interval, and
subtract first frame data from second fame data thereby generating filtered frame data, and
wherein the fall identification module further comprises
a posture detector configured to store target data in a memory unit, to generate an energy profile for each target, and to apply posture selection rules thereby selecting a posture for each target, the posture detector further operable to store a posture history for each target in the memory unit, and
a fall detector configured to access the posture history from the memory unit and to generate a fall alert if at least one target in the monitored region is identified as fallen and no other target in the monitored region is identified as standing.

2. The fall detection system of claim 1 wherein said tracker module comprises a peak detector, an associator and a target tracker wherein:
the peak detector is configured to store filtered frame data, and operable to identify local maxima in each frame thereby generating peak data for the frame;
the associator is configured to store peak data for each frame and to receive tracking data from the target tracker; the associator being operable to associate each peak with a target object, thereby generating target data; and
the target tracker is configured to receive the target data from each frame and operable to populate a target database with a location value and a speed value for each target in each frame, thereby generating tracking data.

3. The fall detection system of claim 1 wherein said processor unit comprises a pre-processor configured and operable to generate energy profiles for target segments of the monitored region and an anomaly detection module configured and operable to identify anomalous energy profiles, the fall detection system further comprising a profile database and wherein the pre-processor comprises an output unit operable to populate the profile database with standard energy profiles and time dependent energy profiles.

4. The fall detection system of claim 3 wherein the anomaly detection module is operable to receive the current energy profile for each target segment from the output unit of the pre-processor and to compare the current energy profile with the corresponding time dependent energy profile stored in the profile database.

5. A fall detection method comprising:
providing at least one radar unit comprising at least one transmitter antenna connected to an oscillator, and at least one receiver antenna configured to receive electromagnetic waves;
providing at least one processor unit configured to receive raw data from the radar unit and operable to generate fall alerts based upon the received data;
providing a communication module configured and operate to communicate a fall alert to third parties;
transmitting electromagnetic waves into a monitored region;
receiving electromagnetic waves reflected from objects in the monitored region;
transferring multiple frames of raw data to processor unit;
removing static objects from the frames of raw data;
identifying moving targets in filtered data;
tracking the moving targets over time;
assigning posture to said targets;
storing a posture history in a memory unit;
applying fall detection rules; and
generating a fall alert if a fall is detected; and
wherein the step of removing static objects from the frames of raw data comprises
collecting raw data from a first frame,
collecting raw data from a second frame, and
subtracting first frame data from the second frame data, and
wherein the step of applying fall detection rules comprises
accessing posture history from the memory unit, and
generating a fall alert only at least one target in the monitored region is identified as fallen and if no other target in the monitored region is identified as standing.

6. The fall detection system of claim 5 wherein the step of identifying moving targets in filtered data comprises:
  detecting local maxima within each frame of filtered data;
  associating each local maximum with a target object.

7. The fall detection system of claim 5 wherein the step of assigning posture to said targets comprises generating an energy profile for each target by assigning:
  a first value for amplitude of reflected energy from an upper region or the target;
  a second value for amplitude of reflected energy from a middle region or the target; and
  a third value for amplitude of reflected energy from a lower region or the target; and
  wherein the step of applying fall detection rules comprises triggering a fall event when any target has an associated third value is higher than both the first value and the second value.

8. The fall detection method of claim 7 further comprising generating a fall alert only if no target is identified having an associated middle value higher than both the first value and the lower value.

9. The fall detection system of claim 5 further comprising:
  generating a set of energy profiles;
  segmenting the monitored region into target segments;
  recording activity within the target region for the duration of a learning period;
  for each target segment recording a time dependent profile distribution by recording the frequency of each energy profile during each hour of the learning period; and
  populating a profile database with standard energy profiles and time dependent energy profiles.

10. The fall detection system of claim 5 further comprising:
  selecting a current profile for each target segment of the monitored region;
  communicating the current profile for each target segment to an anomaly detection module;
  comparing the current profile for each target segment with the time dependent profile distribution stored in the profile database; and
  identifying anomalous energy profiles.

11. The fall detection system of claim 5 further comprising only generating a fall alert if both a fall is detected and an anomalous energy profile is detected.

12. The fall detection system of claim 5 wherein the step of identifying moving targets in filtered data comprises:
  setting a peak detection threshold;
  detecting local maxima within each frame of filtered data;
  defining a stain region for each said local maximum;
  selecting peaks by selecting only local maxima having an amplitude above the peak detection threshold and which do not lie within the stain region of a larger local maximum; and
  associating each selected peak with a target object.

13. The fall detection method of claim 12 wherein the step of tracking the moving targets over time comprises:
  recording a location values for each target in each frame; and
  recording a speed values for each target in each frame.

14. The fall detection method of claim 12 wherein the step of tracking the moving targets over time comprises:
  recording a location values for each target in each frame;
  recording a speed values for each target in each frame;
  predicting an expected value for a target in each frame; and
  comparing expected value for each target with measured value for each target.

15. The fall detection system of claim 5 wherein the step of assigning posture to said targets comprises:
  generating energy profile for each target;
  applying posture selection rules;
  selecting a current posture.

* * * * *